US009516876B2

(12) United States Patent
Inoue

(10) Patent No.: US 9,516,876 B2
(45) Date of Patent: *Dec. 13, 2016

(54) CELL CRYOPRESERVATION TOOL

(71) Applicant: Kitazato BioPharma Co., Ltd., Fuji-shi (JP)

(72) Inventor: Futoshi Inoue, Fujinomiya (JP)

(73) Assignee: KITAZATO BIOPHARMA CO., LTD., Fuji-Shi, Shizuoka (JP)

(*) Notice: Subject to any disclaimer, the term of this patent is extended or adjusted under 35 U.S.C. 154(b) by 13 days.

This patent is subject to a terminal disclaimer.

(21) Appl. No.: 14/349,244

(22) PCT Filed: Oct. 1, 2012

(86) PCT No.: PCT/JP2012/075432
§ 371 (c)(1),
(2) Date: Apr. 2, 2014

(87) PCT Pub. No.: WO2013/051521
PCT Pub. Date: Apr. 11, 2013

(65) Prior Publication Data
US 2015/0044765 A1   Feb. 12, 2015

(30) Foreign Application Priority Data
Oct. 4, 2011 (JP) ................................. 2011-219922

(51) Int. Cl.
*A01N 1/02* (2006.01)
*G01N 1/42* (2006.01)

(52) U.S. Cl.
CPC ........... *A01N 1/0257* (2013.01); *A01N 1/0268* (2013.01); *G01N 1/42* (2013.01)

(58) Field of Classification Search
CPC ....... G01N 1/42; A01N 1/0257; A01N 1/0268
See application file for complete search history.

(56) References Cited

U.S. PATENT DOCUMENTS

2004/0259072 A1   12/2004 Kuwayama et al.
2008/0038155 A1   2/2008 Chian et al.
(Continued)

FOREIGN PATENT DOCUMENTS

CN          1774501 A    5/2006
CN        101087658 A   12/2007
(Continued)

OTHER PUBLICATIONS

Sansinena et al., "Theoretical Prediction of the Effect of Heat Transfer Parameters on Cooling Rates of Liquid-Filled Plastic Straws Used for Cryopreservation of Spermatozoa," CryoLetters, 2010 (month unknown), vol. 31, No. 2, pp. 120-129.
(Continued)

*Primary Examiner* — Gautam Prakash
(74) *Attorney, Agent, or Firm* — Buchanan Ingersoll & Rooney P.C

(57) ABSTRACT

A cell cryopreservation tool has a cell holding member having a body part and a cell holding part and a tubular accommodation member, closed at one end thereof, which is capable of accommodating the cell holding member. The cell holding part of the cell holding member has a long and narrow cell attaching and holding portion. The cell attaching and holding portion has a heat conductor extended in a longitudinal direction thereof. When the cell holding member is accommodated in the tubular accommodation member, the heat conductor is capable of contacting an inner surface of the tubular accommodation member.

12 Claims, 17 Drawing Sheets

(56) References Cited

U.S. PATENT DOCUMENTS

2008/0233633 A1   9/2008   Clairaz et al.
2009/0123992 A1   5/2009   Chin
2011/0196358 A1   8/2011   Criado Scholz

FOREIGN PATENT DOCUMENTS

| JP | 1-277485 A | 11/1989 |
|----|---|---|
| JP | 2000-189155 A | 7/2000 |
| JP | 2002-315573 A | 10/2002 |
| JP | 2004-329202 A | 11/2004 |
| WO | WO 02/085110 A1 | 10/2002 |
| WO | 2007/036628 A1 | 4/2007 |
| WO | 2011/070973 A1 | 6/2011 |

OTHER PUBLICATIONS

Extended European Search Report issued on May 15, 2015, by the European Patent Office in corresponding European Patent Application No. 12838870.9-1660. (5 pages).

International Search Report (PCT/ISA/210) mailed on Jan. 8, 2013, by the Japanese Patent Office as the International Searching Authority for International Application No. PCT/JP2012/075432.

Notification of Transmittal of Translation of the International Preliminary Report on Patentability (Forms PCT/IB338 and PCT/373) and the Written Opinion of the International Searching Authority (Form PCT/ISA 237) dated Apr. 17, 2014, issued in corresponding International Application No. PCT/JP2012/075432. (7 pgs).

CELL CRYOPRESERVATION TOOL

TECHNICAL FIELD

The present invention relates to a cell cryopreservation tool used in cryopreservation cells such as mammalian ova, eggs such as embryos, sperms, and stem cells such as hematopoietic stem cells, pluripotent stem cells, and the like.

BACKGROUND ART

Cryopreservation the mammalian embryo enables conservation of hereditary resources of specific systems and kinds. It is effective for maintaining animals standing on the brink of ruin. It is useful for infertility treatment.

As a method for cryopreservation mammalian embryos, as disclosed in patent document 1 (Japanese Patent Application Laid-Open Publication No. 2000-189155), there is proposed a method for cryopreservation mammalian embryos that mammalian embryos or ova are bonded to the inner surface of the cryopreservation container such as the sterilized frozen straw, frozen vial or frozen tube by using a vitrifying liquid in an amount minimum and enough to enclose the mammalian embryos or the ova therewith. The cryopreservation container is sealed and rapidly cooled by bringing the cryopreservation container into contact with liquid nitrogen. In the thawing method, the cryopreservation container stored in the above method is taken out of the liquid nitrogen and one end thereof is opened. A diluted liquid of 33 to 39 degrees C. is injected directly into the container to thaw the mammalian embryos or the ova and dilute the vitrifying liquid. This method eliminates a possibility that the mammalian embryos or the ova are infected with a disease through viruses or bacteria and is capable of storing them at a high survival rate and thawing them and diluting the vitrifying liquid.

But the operation of bonding eggs such as embryos and ova to the inner surface of the cryopreservation container such as the frozen straw, the frozen vial or the frozen tube with the vitrifying liquid in an amount minimum and enough to enclose them therewith is not easy.

PRIOR ART DOCUMENTS

Patent Documents

Patent document 1: Japanese Patent Application Laid-Open Publication No. 2000-189155

Patent document 2: Japanese Patent Application Laid-Open Publication No. 2004-329202 (US Patent Application Publication No. 2004-0259072)

Patent document 3: Japanese Patent Application Laid-Open Publication No. 2002-315573 (WO 02-085110 A1)

SUMMARY OF THE INVENTION

Problems to be Solved by the Invention

The present applicant also proposed an invention as disclosed in a patent document 2 (Japanese Patent Application Laid-Open Publication No. 2004-329202, US Patent Application Publication No. 2004-0259072). The egg cryopreservation tool 1 of the patent document 2 has the egg cryopreservation tube 2 formed of the liquid nitrogen-resistant material and the metal tubular protective member 3 for protecting the tube 2. The tube 2 has the body part 21 and the egg storing small-diameter part 22 having the inner diameter of 0.1 mm to 0.5 mm. The tube 2 can be heat-sealed at the front side of the small-diameter part and at the body part 21. The tubular protective member 3 has the tubular part 31 storing the front side of the small-diameter part 22 of the tube 2 and the semi-tubular part 32 storing the portion of the small-diameter part 22 not stored in the tubular part 31 and the front portion 21a of the body part 21.

The method for cryopreservation mammalian embryos and the egg cryopreservation tool disclosed in the patent documents 1 and 2 respectively necessitate an operation of accommodating eggs inside the tube to be performed and thus an operation period of time to be spent.

The present applicant proposed an invention as disclosed in a patent document 3 (Japanese Patent Application Laid-Open Publication No. 2002-315573, WO 02-085110 A1). The egg cryopreservation tool 1 of the patent document 3 includes the body part 2 made of the cold-proof material; the egg attaching and holding strip 3, made of the material flexible, transparent, and resistant to liquid nitrogen, which is mounted at one end of the body part 2 and the cylindrical member 4, made of the cold-proof material and sealed at one end thereof, which allows the egg attaching and holding strip 3 to be enclosably and detachably mounted on the body part 2. In the egg cryopreservation tool of the patent document 3, all an operator has to do is to place eggs on the strip, and it is unnecessary to perform an operation of accommodating the eggs inside the tube. Thus the egg cryopreservation tool has an advantage that an egg freezing operation can be easily performed.

But the egg cryopreservation tool of the patent document 3 necessitates the eggs to contact the cooling medium (specifically liquid nitrogen) to vitrify the eggs. Although the contact between the liquid nitrogen and the eggs does not adversely affect the eggs, it is desirable not to bring the eggs into direct contact with the liquid nitrogen.

Therefore it is an object of the present invention to provide a cell cryopreservation tool which allows an operation of placing cells thereon to be easily performed and the cells to be frozen without subjecting the cells to direct contact with a cooling medium.

Means for Solving the Problems

The means for achieving the above-described object is as described below.

A cell cryopreservation tool of the present invention has a cell holding member having a body part formed of a cold-resistant material and a cell holding part formed of the cold-resistant material and a tubular accommodation member, closed at one end thereof, which is capable of accommodating the cell holding member and formed of the cold-resistant material. The cell holding part of the cell holding member has a long and narrow cell attaching and holding portion. The cell attaching and holding portion has a heat conductor extended in a longitudinal direction thereof. When the cell holding member is accommodated in the tubular accommodation member, the heat conductor is capable of contacting an inner surface of the tubular accommodation member.

MODE FOR CARRYING OUT THE INVENTION

Figure 1:
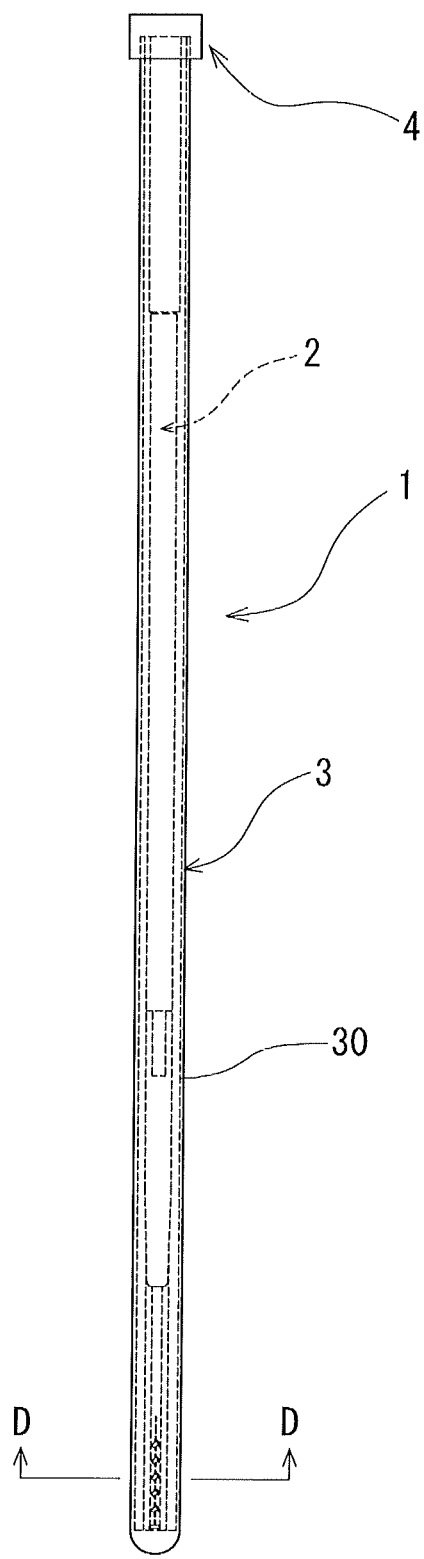
FIG. 1 is a front view of an embodiment of a cell cryopreservation tool of the present invention in which a cell holding member is accommodated in a tubular accommodation member.

The cell cryopreservation tool of the present invention will be described below by using embodiments shown in the drawings.

A cell cryopreservation tool 1 of the present invention has a cell holding member 2 having a body part 23 formed of a cold-resistant material and a cell holding part 21 formed of the cold-resistant material and a tubular accommodation member 3, closed at one end thereof, which is capable of accommodating the cell holding member 2 and formed of the cold-resistant material. The cell holding part 21 of the cell holding member 2 has a long and narrow cell attaching and holding portion (egg attaching and holding portion) 22. The cell attaching and holding portion 22 has heat conductors 25, 26 extended in a longitudinal direction thereof. When the cell holding member 2 is accommodated in the tubular accommodation member 3, the heat conductors 25, 26 are capable of contacting an inner surface of the tubular accommodation member 3.

The cell cryopreservation tool 1 of the present invention is composed of the cell holding member 2 and the tubular accommodation member 3 for accommodating the cell holding member 2 therein. In this embodiment, the cell cryopreservation tool 1 is an egg cryopreservation tool, and the cell holding member 2 is an egg holding member. The cell cryopreservation tool 1 of the present invention can be used to freeze and store cells including eggs such as embryos, ova, sperms, and stem cells such as hematopoietic stem cells, pluripotent stem cells, and the like and particularly the above-described living cells. The cell cryopreservation tool 1 of this embodiment has a lid member 4 to be mounted on an open portion of the tubular accommodation member 3.

Figure 4:
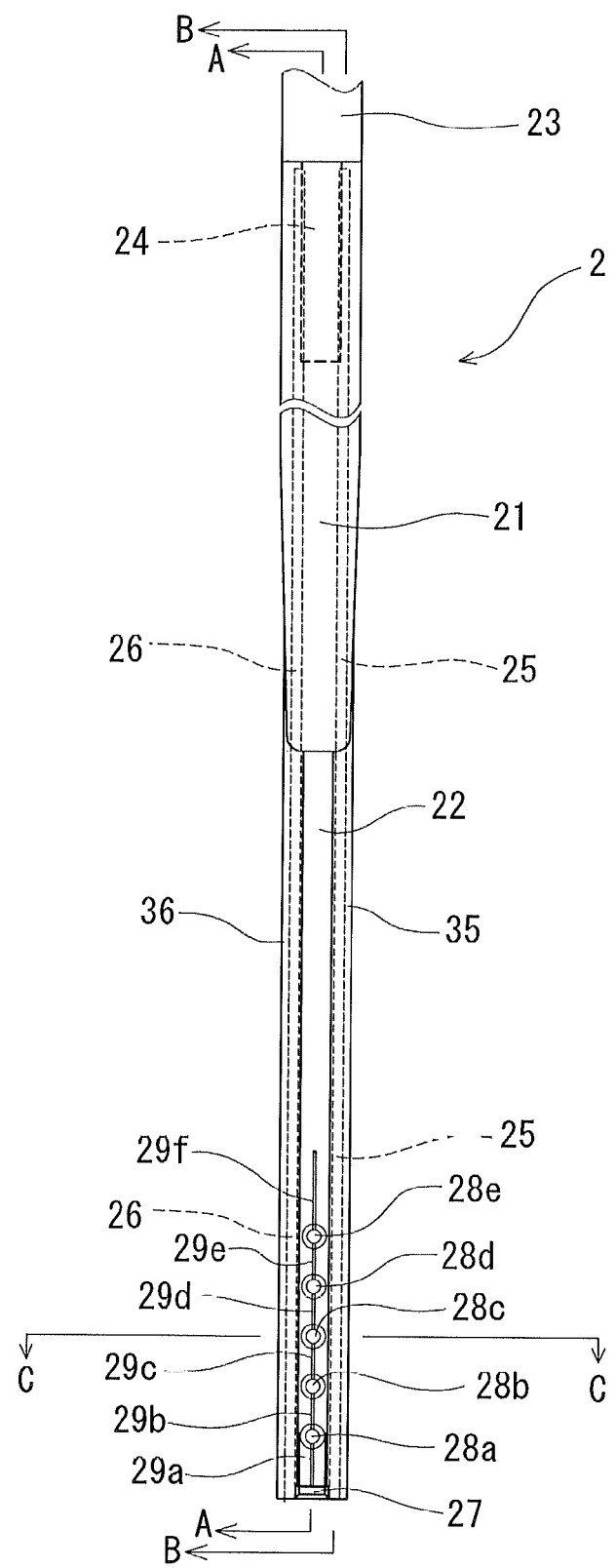
FIG. 4 is an enlarged front view of a distal portion of the cell holding member shown in FIG. 2.
Figure 5:
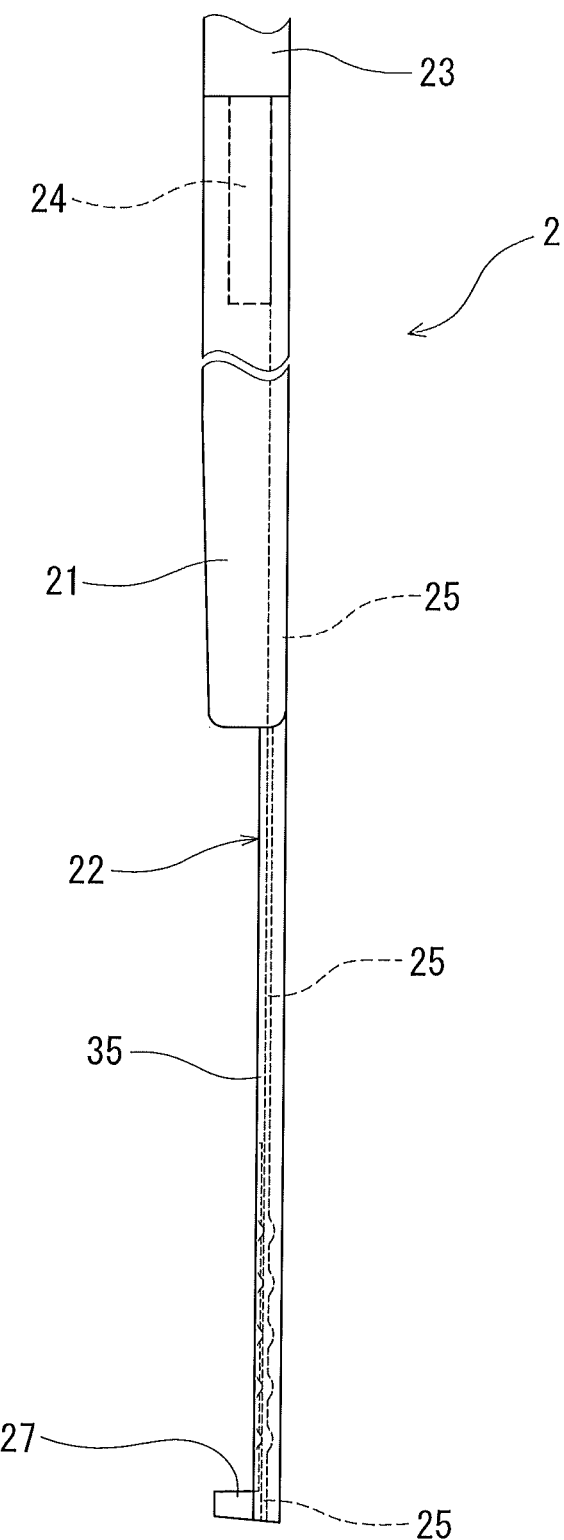
FIG. 5 is a right side view of the cell holding member shown in FIG. 4.
Figure 6:
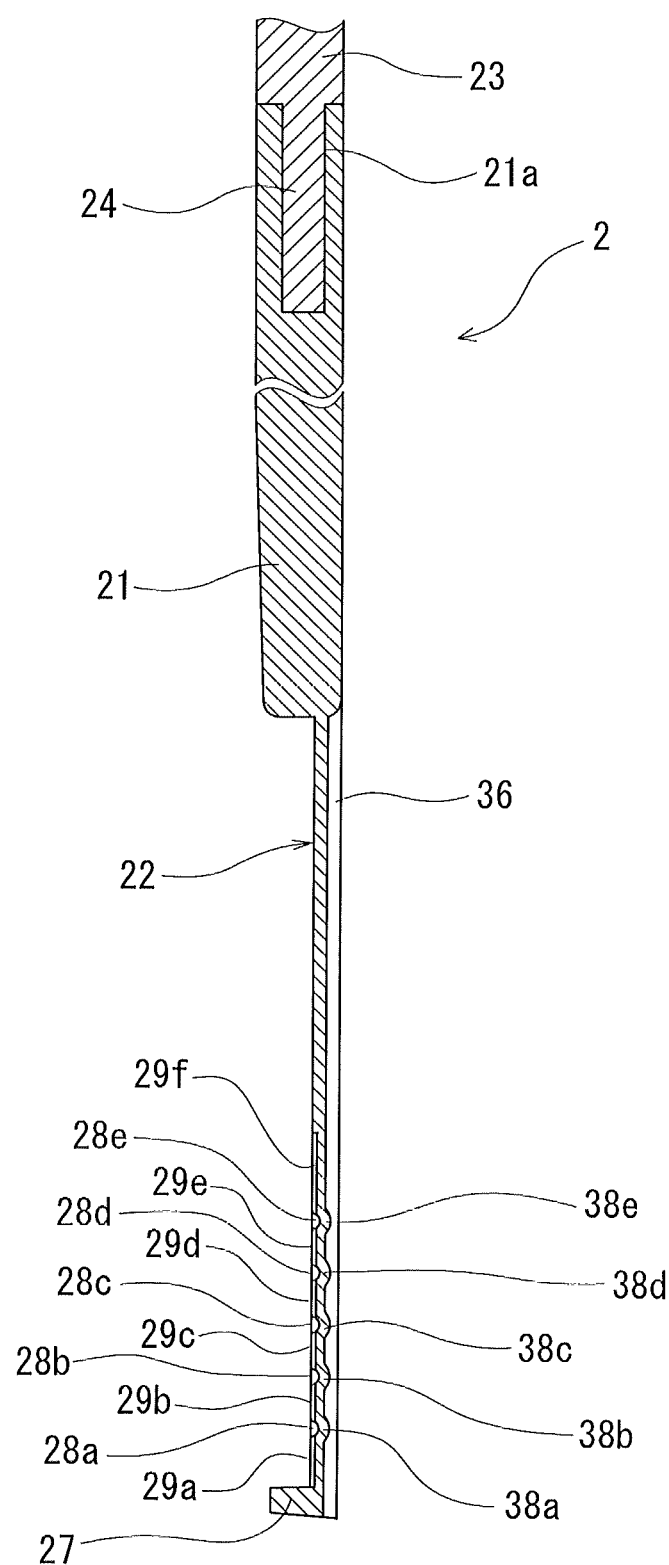
FIG. 6 is a sectional view taken along a line A-A of FIG. 4.
Figure 7:
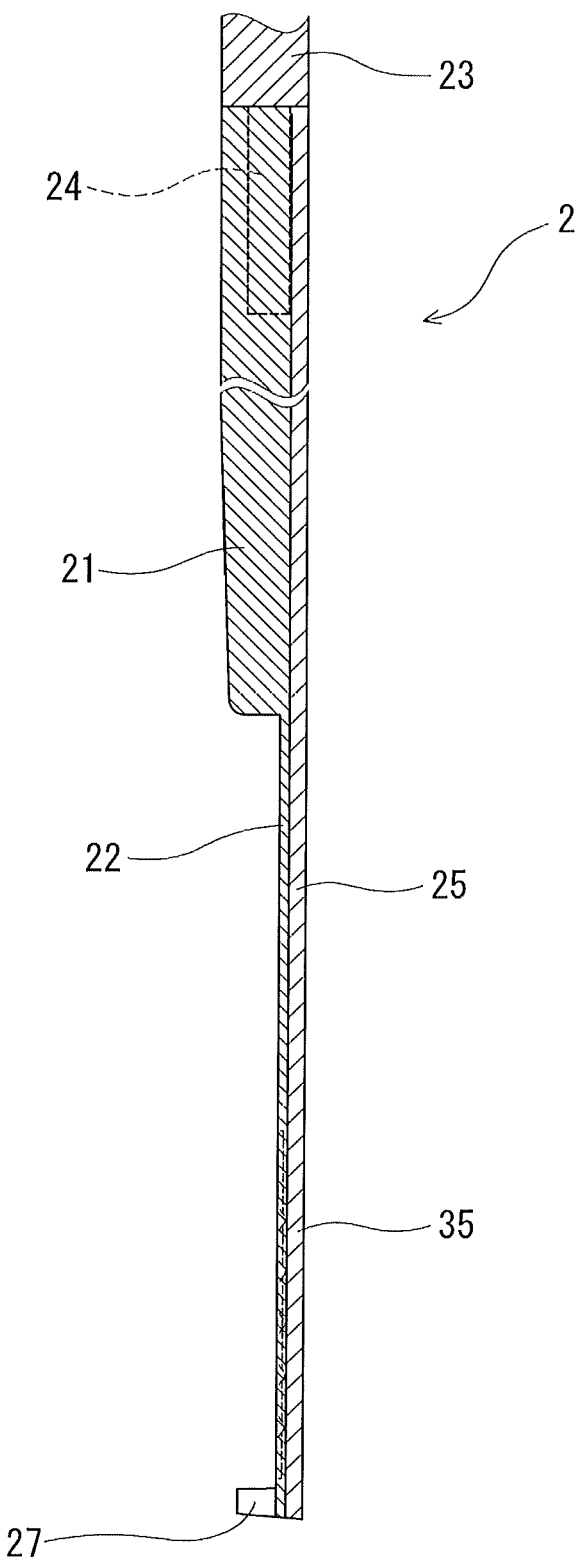
FIG. 7 is a sectional view taken along a line B-B of FIG. 4.

As shown in FIGS. 1, 2, 4 through 9, the cell holding member (more specifically, living cell holding member, egg holding member) 2 has the body part 23 formed of the cold-resistant material and the cell holding part (more specifically, living cell holding part, egg holding part) 21 formed of the cold-resistant material. In the cell holding member of this embodiment, as shown in FIGS. 4 through 6 (particularly FIG. 6), a hole portion 21*a* extended a predetermined length toward a distal side of the cell holding part 21 is formed at a proximal portion thereof. A projected portion 24, extended a predetermined length, which is capable of penetrating into the hole portion 21*a* is formed at a distal portion of the body part 23. The projected portion 24 of the body part 23 is inserted into the hole portion 21*a* of the cell holding part 21 to fix both portions 24 and 21*a* to each other.

The cell holding part 21 has an approximately rectangular cross section. As described above, the cell holding part 21 has the proximal portion connected with the body part 23 and the cell attaching and holding portion 22 projected from the proximal portion thereof toward the distal side thereof. In the cell holding member of this embodiment, the cell attaching and holding portion 22 has the shape of a long and narrow belt. The surface of the cell attaching and holding portion forms a cell attaching and holding surface (egg attaching and holding surface).

Figure 8:
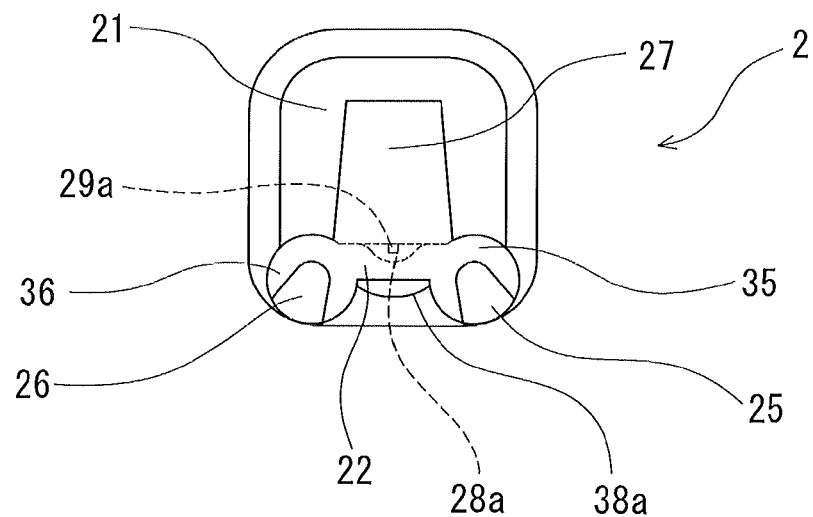
FIG. 8 is an enlarged bottom view of the cell holding member shown in FIG. 4.
Figure 9:
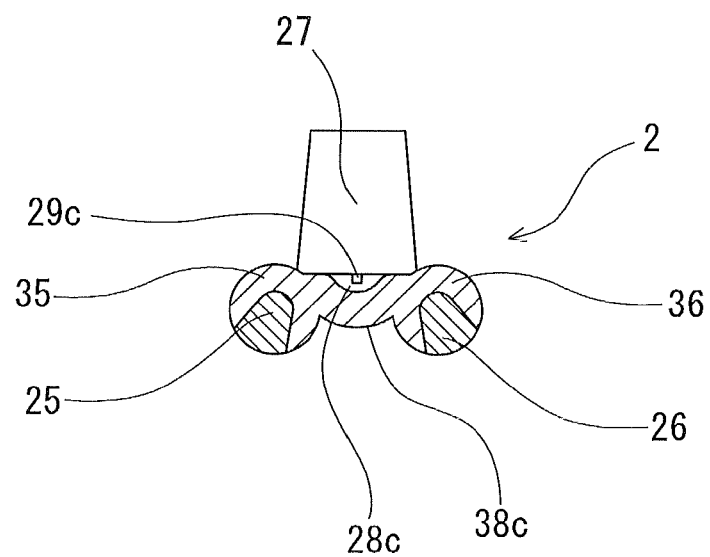
FIG. 9 is an explanatory view for explaining a section obtained by cutting the cell holding member along a line C-C of FIG. 4.

As shown in FIGS. 4 through 9, in the cell holding member 2 of this embodiment, a cell accommodation concave portion (specifically, living cell accommodation concave portion, egg accommodation concave portion) is formed on the surface of the cell attaching and holding portion 22. In this embodiment, a plurality of cell accommodation concave portions (living cell accommodation concave portions, egg accommodation concave portions) 28a, 28b, 28c, 28d, and 28e is formed on the surface of the cell attaching and holding portion 22 in its longitudinal direction. As shown in FIGS. 6 and 9, each of the cell accommodation concave portions 28a, 28b, 28c, 28d, and 28e is formed as an approximately hemispherical concave portion. The concave portions 28a, 28b, 28c, 28d, and 28e are linearly arranged on the cell attaching and holding portion 22 from a position spaced at a predetermined interval from the distal end of the cell holding member 2 toward the proximal side thereof. The concave portions are spaced at almost regular intervals. Although a plurality of the concave portions is formed in this embodiment, the formation of one concave portion is allowed. In the case where a plurality of the concave portions is formed, it is preferable to form two to eight concave portions. It is preferable to set the depth of each concave portion to 0.05 to 0.5 mm and the diameter of an opening to be formed on the upper surface thereof to 0.1 to 0.5 mm. It is preferable to set the spaced interval between the adjacent concave portions to 1 to 3 mm. In the cell holding member of this embodiment, bulged portions 38a, 38b, 38c, 38d, and 38e are formed on a backside of a portion of the cell attaching and holding portion 22 where the cell accommodation concave portions 28a, 28b, 28c, 28d, and 28e are formed. Thus the portion of the cell attaching and holding portion where the cell accommodation concave portions are formed is not thin, but has a sufficient strength. The surface of the cell cryopreservation tool 1 may be formed as a flat surface without forming the cell accommodation concave portions to use the formed flat surface thereof as the cell attaching and holding portion. It is preferable to set the width of the cell attaching and holding portion 22 to 0.4 to 1.0 mm, its length to 5 to 30 mm, and its entire thickness and its thickness at the concave portions to 0.08 to 1.0 mm. It is preferable to set the length of the thick proximal portion of the cell holding part 21 to 5 to 30 mm and the length of the body part to 20 to 100 mm.

Figure 12:
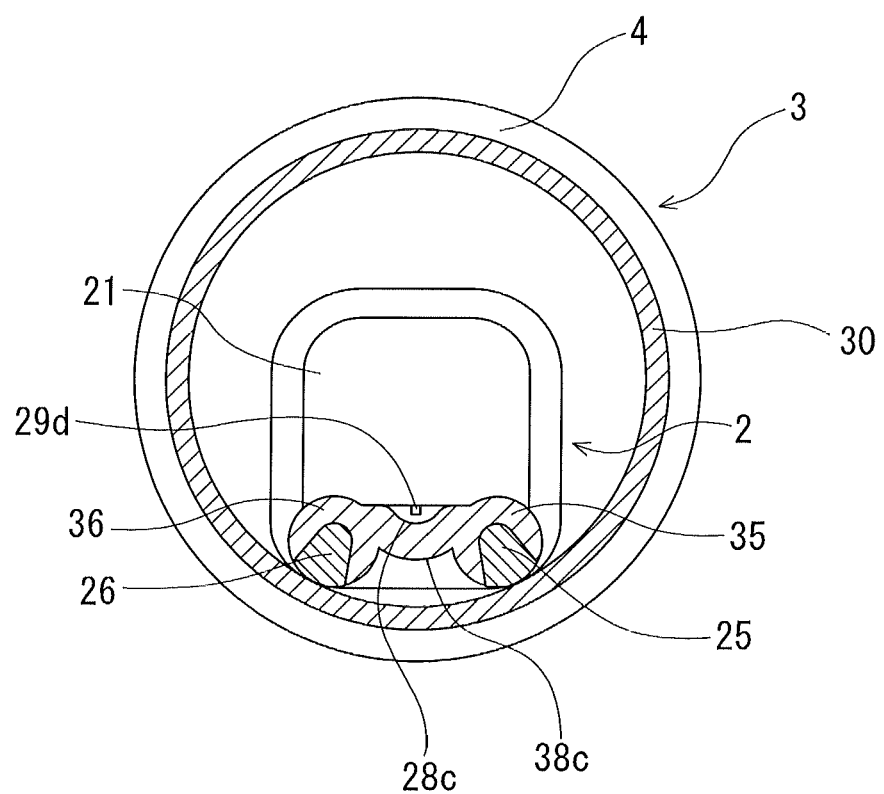
FIG. 12 is a sectional view taken along a line D-D of FIG. 1.

As shown in FIGS. 4 through 9, in the cell holding member 2 of the present invention, the cell attaching and holding portion 22 has the heat conductors 25, 26 extended in the longitudinal direction thereof. In the cell holding member 2 of this embodiment, one of the heat conductors 25, 26 is formed at one side of the cell attaching and holding portion 22, whereas the other heat conductor is formed at the other side thereof. The heat conductor may be formed at only one side of the cell attaching and holding portion 22. The heat conductors 25, 26 are essentially disposed at one side or both sides (both sides in this embodiment) of the portion of the cell attaching and holding portion 22 where the cell accommodation concave portions 28a, 28b, 28c, 28d, and 28e are formed. In addition, the distal end surfaces of the heat conductors 25, 26 are exposed to the outside at the distal end surface of the cell attaching and holding portion 22. Thus a plurality of the egg accommodation concave portions 28a, 28b, 28c, 28d, and 28e is positioned between the two heat conductors 25, 26. In the cell holding member of this embodiment, a part of the axially extended side surface of each of the heat conductors 25, 26 is exposed to the outside and is thus capable of contacting the inner surface of the tubular accommodation member 3, namely, the inner surface of a tubular body 30 having a cell holding member accommodation portion 31 formed inside it, as shown in FIG. 12. Thereby heat conduction is satisfactorily accomplished through the tubular accommodation member 3. In the cell holding member of this embodiment, a part of each of the heat conductors 25, 26 is exposed to the outside, whereas the other part (unexposed part) thereof is embedded in the cell attaching and holding portion 22.

In this embodiment, the heat conductors 25, 26 are formed of a linear member or a narrow bar-shaped member. The distal end surface of each heat conductor and a part of the side thereof are exposed.

As shown in FIGS. 8 and 9, the cell holding member 2 of this embodiment has two side bulged portions 35, 36, one of which is formed at one side of the portion of the cell attaching and holding portion 22 where the cell accommodation concave portions 28a, 28b, 28c, 28d, and 28e are formed and the other of which is formed at the other side of the above-described portion. The two side bulged portions are extended in the longitudinal direction of the cell attaching and holding portion 22. Because the cell holding member 2 has the bulged portion at both sides of the cell accommodation concave portions, it is possible to securely restrain the cells from moving to the sides of the cell accommodation concave portions when the cells are placed thereon and in addition prevent the cells from separating therefrom. Thus in this embodiment, the belt-shaped portion connects the two bulged portions 35, 36 to each other. The cell accommodation concave portions 28a, 28b, 28c, 28d, and 28e are formed on the belt-shaped portion.

Figure 10:
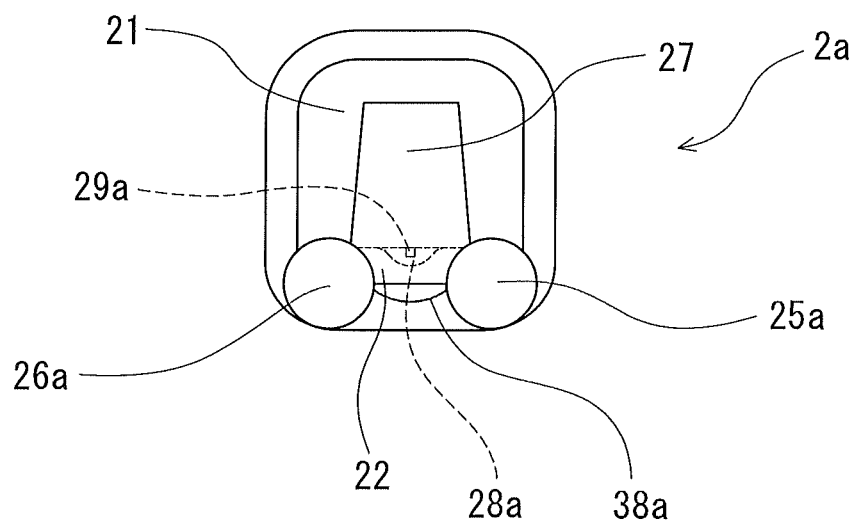
FIG. 10 is an enlarged bottom view of a cell holding member for use in a cell cryopreservation tool of another embodiment of the present invention.
Figure 11:
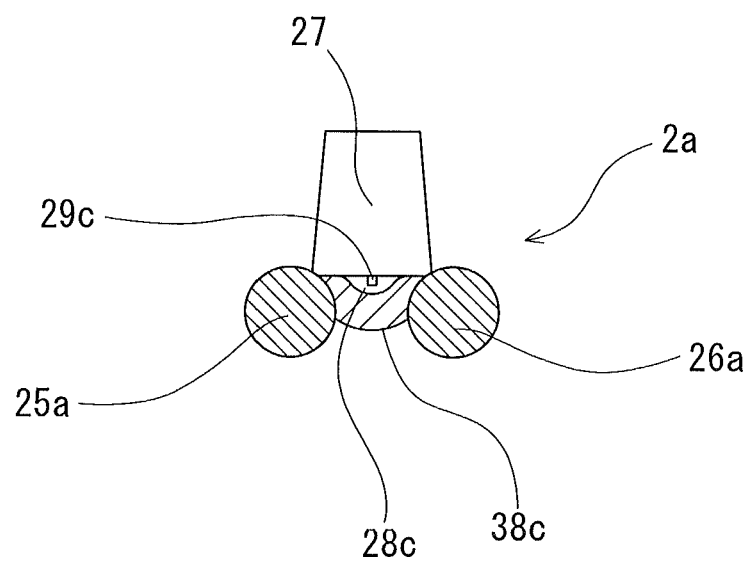
FIG. 11 is an explanatory view for explaining a sectional construction of the cell holding member shown in FIG. 10.

Like a cell holding member 2a shown in FIGS. 10 and 11, the entire bulged portion may be formed of heat conductors 25a, 26a. In this embodiment, one of the heat conductors 25a, 26a is formed at one side of the portion of the cell attaching and holding portion 22 where the cell accommodation concave portions 28a, 28b, 28c, 28d, and 28e are formed and the other of the heat conductors is formed at the other side of the above-described portion. The heat conductors 25a, 26a are extended in the longitudinal direction of the cell attaching and holding portion 22 to form the two side bulged portions. The heat conductors 25a, 26a are mostly exposed to the outside.

As shown in FIGS. 4 through 9, in the cell holding member 2 of this embodiment, the cell attaching and holding portion 22 has a projected portion 27 formed at a position thereof nearer to the distal end thereof than the cell accommodation concave portions 28a, 28b, 28c, 28d, and 28e. The projected portion 27 is projected from the distal end of the cell attaching and holding portion 22 toward an upper surface side (the side at which the cell accommodation concave portions are formed) thereof. As shown in FIG. 6, the distal end surface of the projected portion 27 is formed as an inclined surface inclining a little toward the proximal side of the cell attaching and holding portion. By forming the projected portion 27 having the above-described construction, it is possible to prevent the cells from falling from the cell holding member 2, in other words, from the cell attaching and holding portion 22, if the cells separate from the cell accommodation portion and move toward the distal side of the cell attaching and holding portion. In the cell holding member 2 of this embodiment, as described above, in cooperation between the projected portion 27 and the side bulged portions 35, 36, one of which is formed at one side of the cell attaching and holding portion 22 and the other of which is formed at the other side thereof, the cells are prevented from falling from the cell attaching and holding portion.

As shown in FIGS. 4 through 9, in the cell holding member 2 of this embodiment, the cell attaching and holding portion 22 has groove portions 29a, 29b, 29c, 29d, 29e, and 29f which communicate with the cell accommodation concave portions 28a, 28b, 28c, 28d, and 28e and are extended in the longitudinal direction of the cell attaching and holding portion 22. In the cell holding member of this embodiment, each of the groove portions 29a, 29b, 29c, 29d, and 29e communicates the adjacent cell accommodation concave portions to each other. More specifically, the groove portion 29b communicates the concave portions 28a and 28b to each other. The groove portion 29c communicates the concave portions 28b and 28c to each other. The groove portion 29d communicates the concave portions 28c and 28d to each other. The groove portion 29e communicates the concave portions 28d and 28e to each other.

As shown in FIG. 6, in this embodiment, the cell attaching and holding portion 22 has the groove portion 29a extended toward the distal end thereof from the cell accommodation concave portion 28a positioned nearer to the distal end thereof than any other cell accommodation concave portions. The distal end of the groove portion 29a reaches the above-described projected portion or is extended to the vicinity thereof. In the cell holding member of this embodiment, the cell attaching and holding portion 22 has the groove portion 29f extended toward the proximal end thereof from the cell accommodation concave portion 28e positioned nearer to the proximal end thereof than any other cell accommodation concave portions.

By forming the groove portions, having the above-described construction, which communicate with the cell accommodation concave portions, an excess amount of a cryopreservation liquid accommodated in the cell accommodation concave portions together with the cells flows into the groove portions. Thereby it is possible to prevent the cells from being coated with the excess amount of the cryopreservation liquid and rapidly freeze the cells. In addition, because the adjacent cell accommodation concave portions communicate with each other through the groove portion, the cryopreservation liquid is capable of moving easily from the cell accommodation concave portions to the groove portions. Further an equal amount of the cryopreservation liquid remains in a plurality of the cell accommodation concave portions. It is preferable to set the width of each groove portion to 100 μm to 500 μm and the depth thereof to 50 μm to 500 μm.

The heat conductor is not limited to the above-described linear or narrow bar-shaped member, but may consist of a plate-shaped member. Two plate-shaped members may be disposed on the cell attaching and holding portion like the heat conductors 25, 26.

The body part 23 and the cell holding part 21 are formed of the cold-resistant material. It is preferable to form the body part 23 and the cell holding part 21 of a liquid nitrogen-resistant material. In other words, it is preferable to form them of a material which does not brittle when the material contacts liquid nitrogen. It is preferable that the cell holding part 21 is transparent or semitransparent and in addition flexible to some extent. As materials which form the body part 23 and the cell holding part 21, synthetic resins such as 3-polyethylene fluoride, low-density polyethylene, medium-density polyethylene, high-density polyethylene, polycarbonate, nylon, polysulfone, polyester, polystyrene, polyimide, ultra-high-molecular-weight polyethylene, ethylene-vinyl acetate copolymer; and laminates of films formed of these synthetic resins are preferably used.

The heat conductors 25, 26 are formed of a heat conductive material. As the heat conductive material, metals such as silver, copper, aluminum, and stainless steel; thermally conductive ceramics such as aluminum nitride, silicon nitride, and alumina; metal powder; thermally conductive ceramic powder such as aluminum nitride; and a thermally conductive resin containing a highly thermally conductive substance such as carbon fiber can be preferably used.

Figure 2:
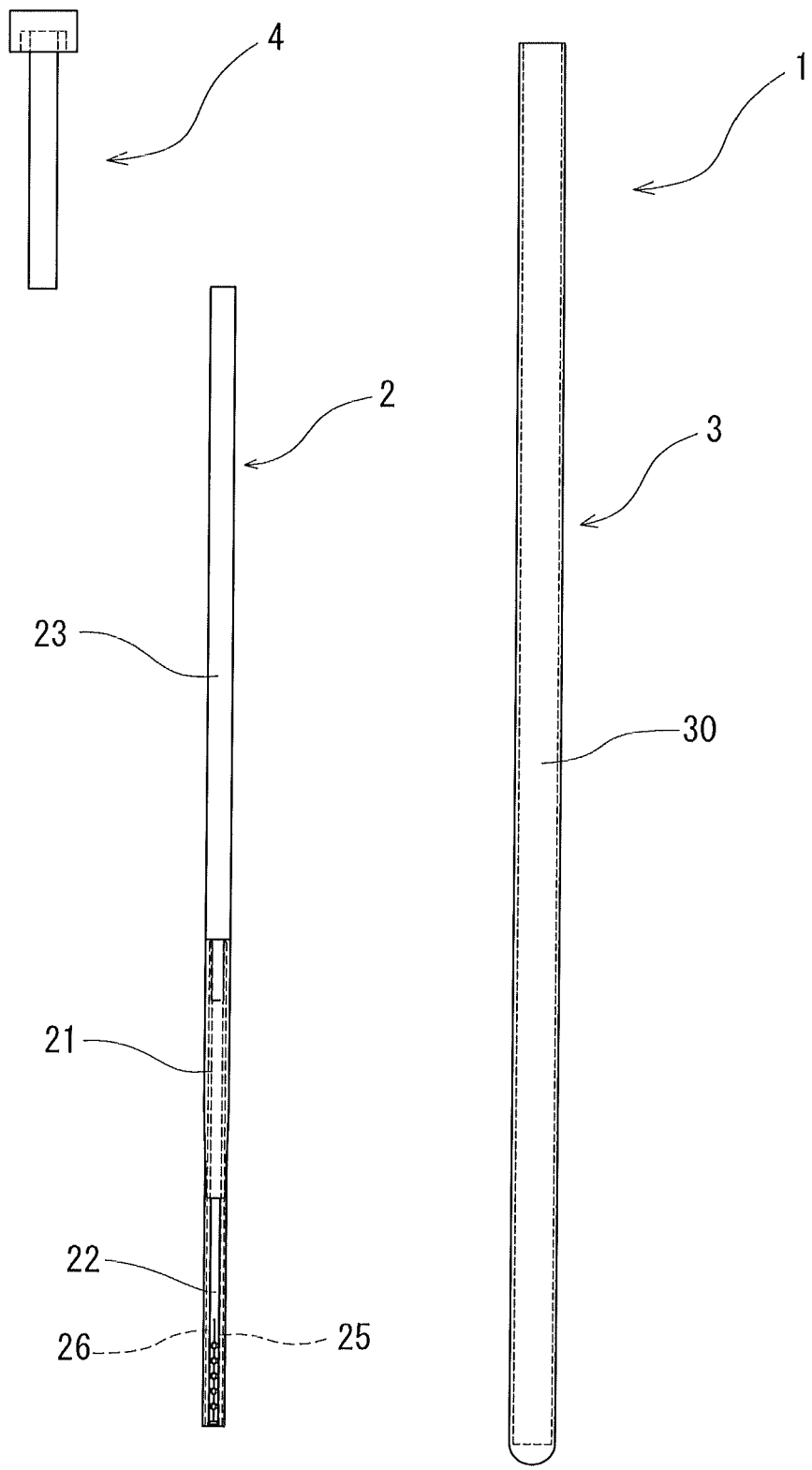
FIG. 2 is a front view of an embodiment of the cell cryopreservation tool of the present invention in which the cell holding member is not accommodated in the tubular accommodation member.
Figure 3:
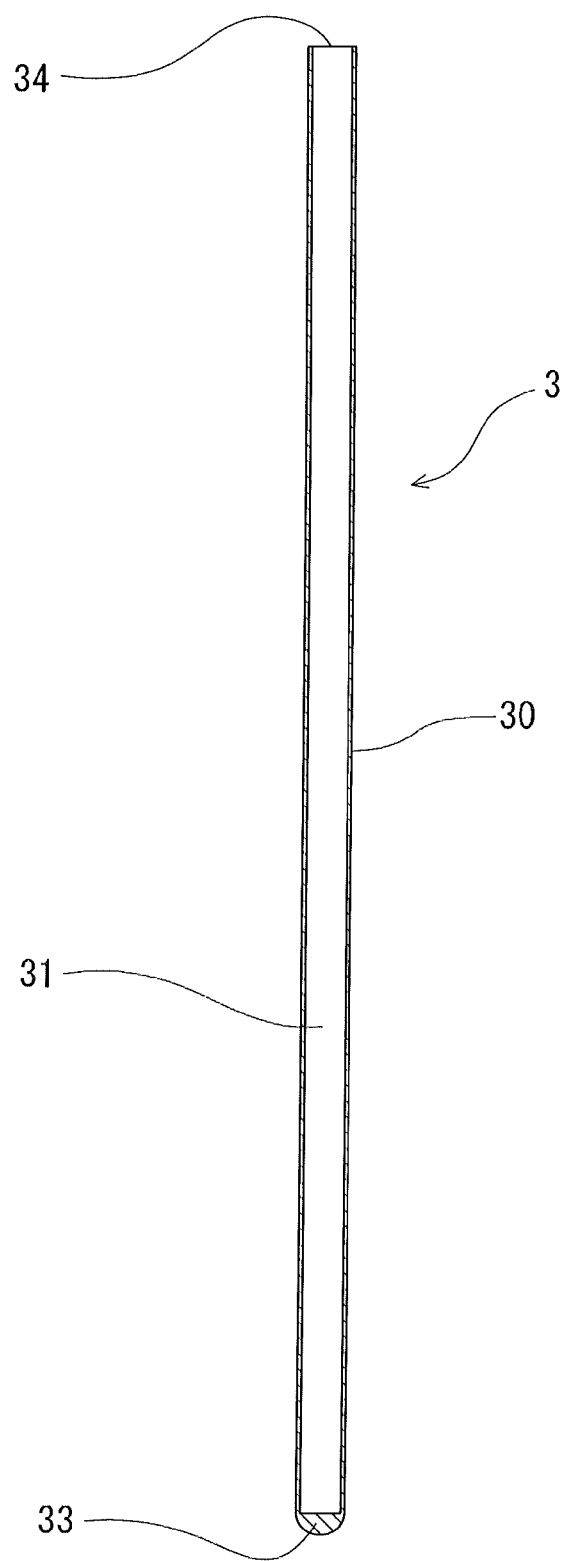
FIG. 3 is a longitudinal sectional view of the tubular accommodation member shown in FIG. 2.

As shown in FIGS. 1 through 3, the tubular accommodation member 3 is a tubular body, one end of which is closed, which is capable of accommodating the cell holding member 2 and made of the cold-resistant material. The tubular accommodation member 3 is a tubular body 30 having a distal-end closed portion 33, a proximal-end open portion 34, and the cell holding member accommodation portion 31 formed inside it.

Figure 13:
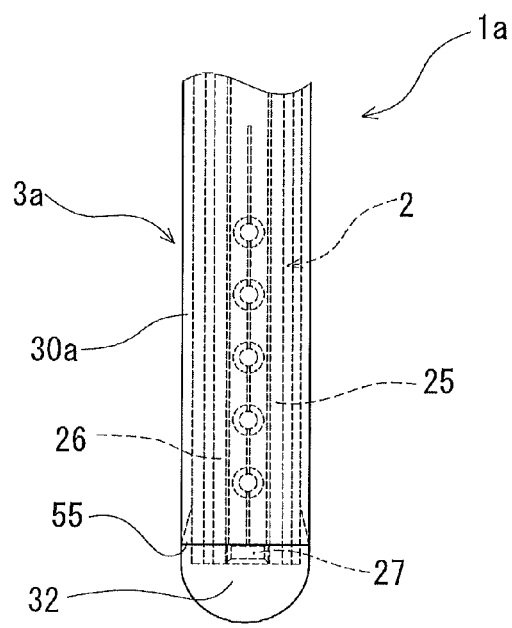
FIG. 13 is an enlarged front view of a distal portion of a cell cryopreservation tool of still another embodiment of the present invention.
Figure 14:
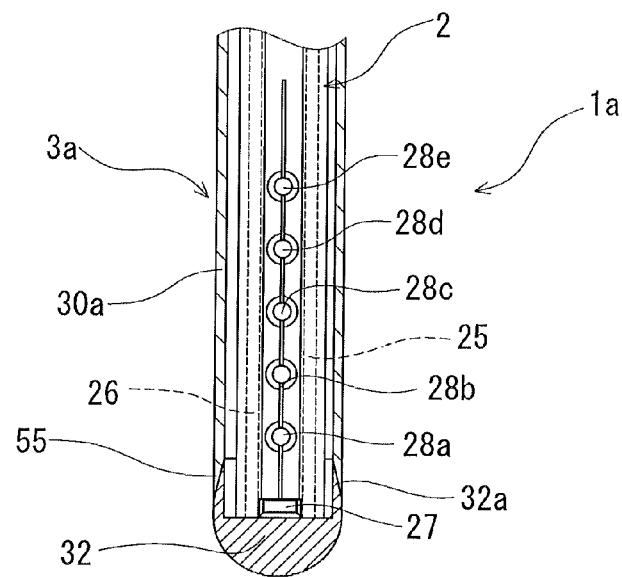
FIG. 14 is an explanatory view for explaining a sectional construction of a tubular accommodation member of the cell cryopreservation tool shown in FIG. 13.

It is preferable for the tubular accommodation member of this embodiment to have a heat conductive member. In a cell cryopreservation tool 1a of an embodiment shown in FIGS. 13 and 14, a tubular accommodation member 3a has a heat conductive member 32 provided at a distal end of a tubular body 30a. The tubular accommodation member 3a has the heat conductive member 32 fixed to the open distal end of the tubular body 30a. The inner surface of the heat conductive member 32 is exposed to the inside of the tubular accommodation member 3a and capable of contacting the exposed distal end surface of each of the heat conductors 25, 26 of the cell holding member 2. The heat conductive member 32 has a short tubular portion 32a forming a concave portion. The outer surface of the tubular portion 32a tapers off. Thus the diameter of the tubular portion 32a becomes gradually smaller toward its proximal end. In correspondence to the tapered configuration of the tubular portion 32a, the inner diameter of an open portion 55 of the tubular accommodation member 3a increases toward its open distal end. The tubular portion 32a of the heat conductive member 32 is inserted into the open portion 55 of the tubular accommodation member 3a to fix the tubular portion 32a thereto. In the tubular accommodation member of this embodiment, the outer surface of the heat conductive member 32 mounted on the tubular accommodation member 3a is exposed to the outside. The heat conductive member 32 may be accommodated inside the tubular accommodation member 3a.

Figure 23:
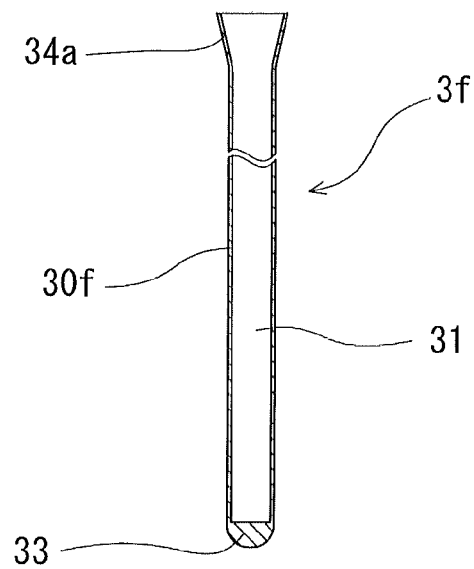
FIG. 23 is a partly abbreviated front view of a tubular accommodation member to be used for a cell cryopreservation tool of still another embodiment of the present invention.
Figure 24:
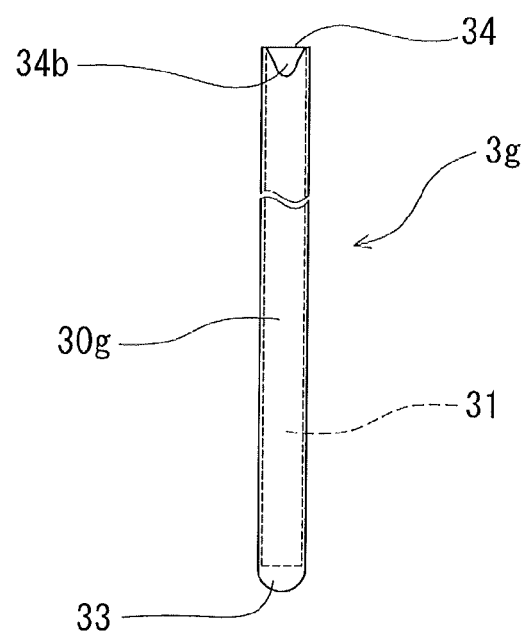
FIG. 24 is a partly abbreviated front view of a tubular accommodation member to be used for a cell cryopreservation tool of still another embodiment of the present invention.
Figure 25:
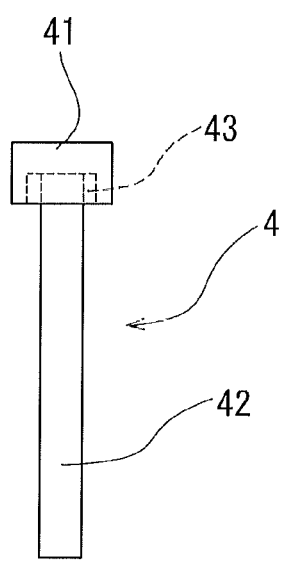
FIG. 25 is a front view of a lid member to be used for the cell cryopreservation tool of the present invention.
Figure 26:
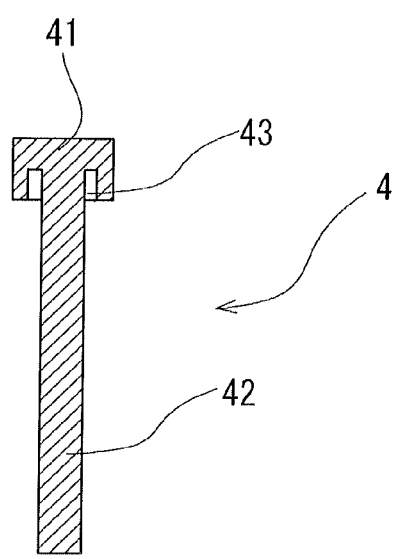
FIG. 26 is a longitudinal sectional view of the lid member shown in FIG. 25.

As the tubular accommodation member, like a tubular accommodation member 3f shown in FIG. 23, a proximal-end open portion of a tubular body 30f thereof may be formed as a diameter-increased proximal-end open portion 34a whose diameter increases toward its proximal end. Like a tubular accommodation member 3g shown in FIG. 24, a tubular body 30g thereof may have a cut-out portion 34b formed at its proximal-end open portion 34. By forming the diameter-increased portion or the cut-out portion on the tubular accommodation member, the cell holding member 2 can be easily inserted thereinto.

The tubular body 30 is formed of the cold-resistant material. It is preferable to form the tubular body 30 of a liquid nitrogen-resistant material. In other words, it is preferable to form the tubular body of a material which does not brittle when the material contacts liquid nitrogen. It is preferable that the tubular body 30 is transparent so that its inside is visually recognizable or semitransparent. As materials which form the tubular body 30, synthetic resins such as 3-polyethylene fluoride, low-density polyethylene, medium-density polyethylene, high-density polyethylene, polycarbonate, nylon, polysulfone, polyester, polystyrene, polyimide, ultra-high-molecular-weight polyethylene, ethylene-vinyl acetate copolymer; and laminates of films formed of these synthetic resins are preferably used.

It is preferable to set the length of the cell holding member accommodation portion 31 of the tubular accommodation member 3 longer than the overall length of the cell holding member 2 by 10 to 50 mm. It is preferable to set the overall length of the tubular accommodation member (tubular body 30) 3 to 50 to 150 mm and the inner diameter thereof to 2 to 5 mm.

The heat conductive member 32 is formed of a heat conductive material. As the heat conductive material, metals such as silver, copper, aluminum, and stainless steel; thermally conductive ceramics such as aluminum nitride, silicon nitride, and alumina; metal powder; thermally conductive ceramic powder such as aluminum nitride; and a thermally conductive resin containing a highly thermally conductive substance such as carbon fiber are preferably used.

Figure 15:
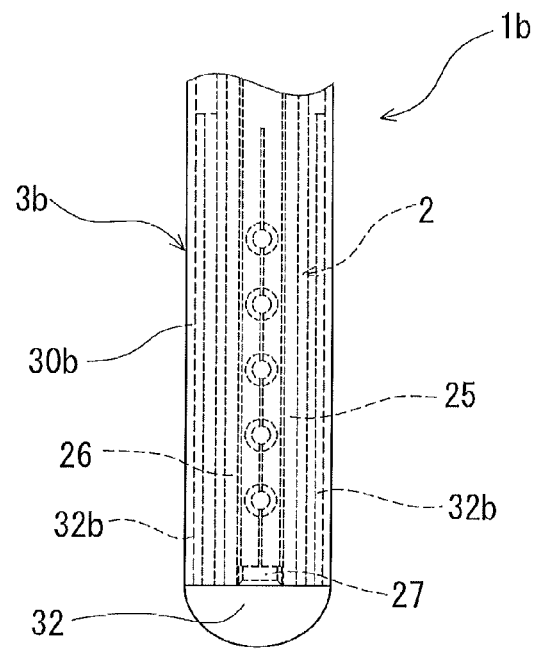
FIG. 15 is an enlarged front view of a distal portion of a cell cryopreservation tool of still another embodiment of the present invention.
Figure 16:
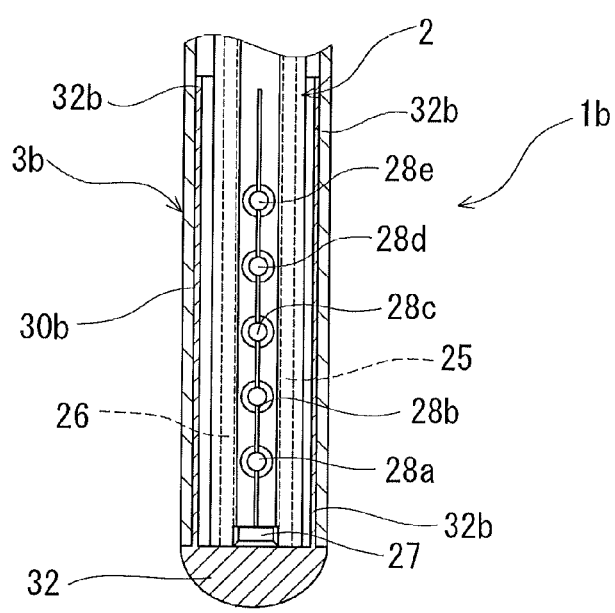
FIG. 16 is an explanatory view for explaining a sectional construction of a tubular accommodation member of the cell cryopreservation tool shown in FIG. 15.

The mode of the heat conductive member to be mounted on the tubular accommodation member 3 is not limited to the above-described one, but like a cell cryopreservation tool 1b of an embodiment shown in FIGS. 15 and 16, the heat conductive member 32 has a tubular portion 32b which is fixed (specifically, closes open distal end) to a distal end of a tubular body 30b of a tubular accommodation member 3b and extended a predetermined length inside the tubular body 30b. As shown in FIG. 16, the length of the tubular portion 32b is so set that the tubular portion 32b is capable of enclosing the portion of the cell holding member 2 where the cell accommodation concave portions are formed, when the cell holding member 2 is accommodated inside the tubular accommodation member 3b. In this embodiment, the exposed side surfaces of the heat conductors 25, 26 are capable of contacting the inner surface of the tubular portion 32b of the heat conductive member 32.

Figure 17:
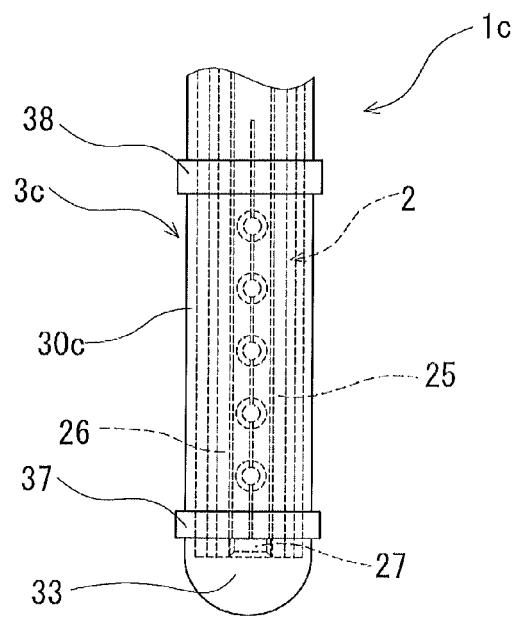
FIG. 17 is an enlarged front view of a distal portion of a cell cryopreservation tool of still another embodiment of the present invention.
Figure 18:
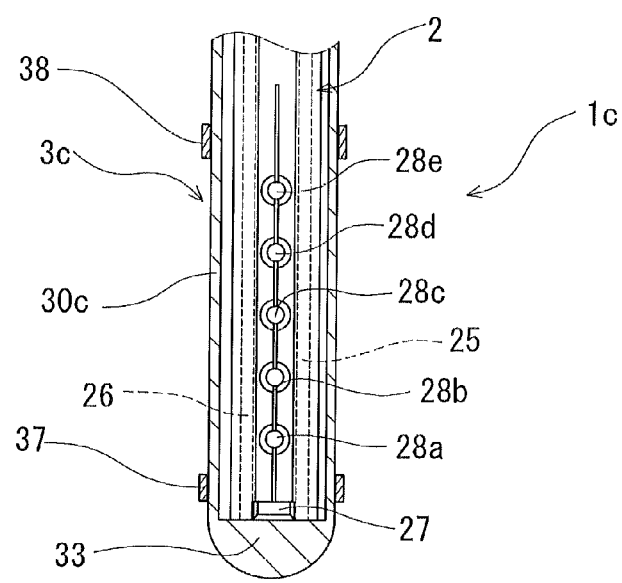
FIG. 18 is an explanatory view for explaining a sectional construction of a tubular accommodation member of the cell cryopreservation tool shown in FIG. 17.

As a mode of the heat conductive member, like a cell cryopreservation tool 1c of an embodiment shown in FIGS. 17 and 18, the heat conductive member may be a ring-shaped one fixed to the side surface of a tubular accommodation member 3c. In this embodiment, as shown in FIGS. 17 and 18, when the cell holding member 2 is accommodated in the tubular accommodation member 3c, ring-shaped heat conductive members 37, 38 are fixed to a portion, of a tubular body 30c, which partly or entirely encloses the portion of the cell holding member 2 where the cell accommodation concave portions are formed. The ring-shaped heat conductive members 37, 38 are located at positions where the heat conductive members 37, 38 do not prevent visual recognition of the cell accommodation concave portions from the outside. More specifically, when the cell holding member 2 is accommodated inside the tubular accommodation member 3c, the heat conductive member 37 disposed at the distal side of the tubular accommodation member is fixed to the outer surface of the tubular body 30c at a position thereof disposed nearer to the distal end thereof than the portion of the cell holding member 2 where the cell accommodation concave portions are formed. When the cell holding member 2 is accommodated inside the tubular accommodation member 3c, the heat conductive member 37 disposed at the proximal side of the tubular accommodation member is fixed to the outer surface of the tubular body 30c at a position thereof disposed nearer to the distal end thereof than the portion of the cell holding member 2 where the cell accommodation concave portions are formed.

The heat conductive member may be formed as a tubular member almost entirely enclosing the portion of the cell holding member 2 where the cell accommodation concave portions are formed, although the heat conductive member prevents visual recognition of the cell accommodation concave portions from the outside.

Figure 19:
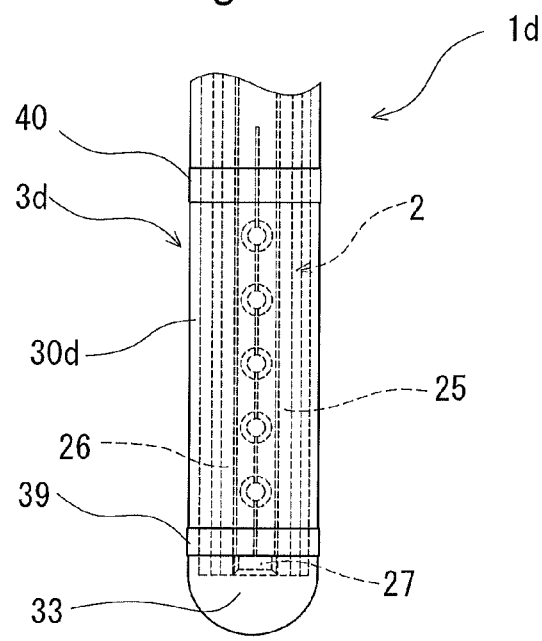
FIG. 19 is an enlarged front view of a distal portion of a cell cryopreservation tool of still another embodiment of the present invention.
Figure 20:
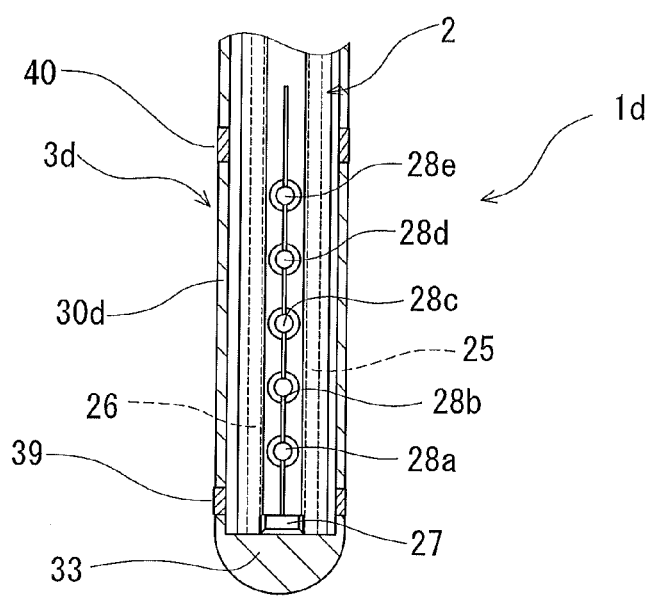
FIG. 20 is an explanatory view for explaining a sectional construction of a tubular accommodation member of the cell cryopreservation tool shown in FIG. 19.

As a mode of the heat conductive member, like a cell cryopreservation tool 1d of an embodiment shown in FIGS. 19 and 20, the heat conductive member may be a ring-shaped one embedded in the side surface of a tubular accommodation member 3d. In this embodiment, as shown in FIGS. 19 and 20, when the cell holding member 2 is accommodated in the tubular accommodation member 3d, ring-shaped heat conductive members 39, 40 are embedded in a portion, of a tubular body 30d, which partly or entirely encloses the portion of the cell holding member 2 where the cell accommodation concave portions are formed. The ring-shaped heat conductive members 39, 40 are located at positions where the heat conductive members 39, 40 do not prevent visual recognition of the cell accommodation concave portions from the outside. More specifically, when the cell holding member 2 is accommodated in the tubular accommodation member 3d, the heat conductive member 39 disposed at the distal side of the tubular accommodation member is embedded in the tubular body 30d at a position thereof disposed nearer to the distal end thereof than the portion of the cell holding member 2 where the cell accommodation concave portions are formed. When the cell holding member 2 is accommodated in the tubular accommodation member 3d, the heat conductive member 40 disposed at the proximal side of the tubular accommodation member is embedded in the tubular body 30d at a position thereof nearer to the distal end thereof than the portion of the cell holding member 2 where the cell accommodation concave portions are formed. The ring-shaped heat conductive members 39, 40 embedded in the tubular body 30d are exposed at the inner surface of the tubular accommodation member 3d and are capable of contacting the exposed side surfaces of the heat conductors 25, 26.

The conductive members may be formed as a tubular member almost entirely enclosing the portion of the cell holding member 2 where the cell accommodation concave portions are formed, although the heat conductive member prevents visual recognition of the cell accommodation concave portions from the outside.

Figure 21:
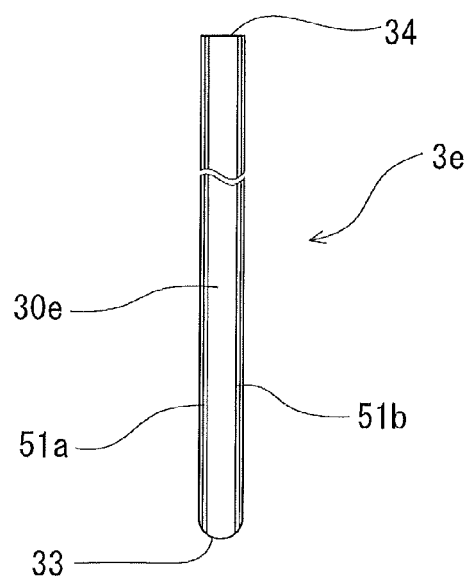
FIG. 21 is a partly abbreviated enlarged front view of a tubular accommodation member to be used for a cell cryopreservation tool of still another embodiment of the present invention.
Figure 22:
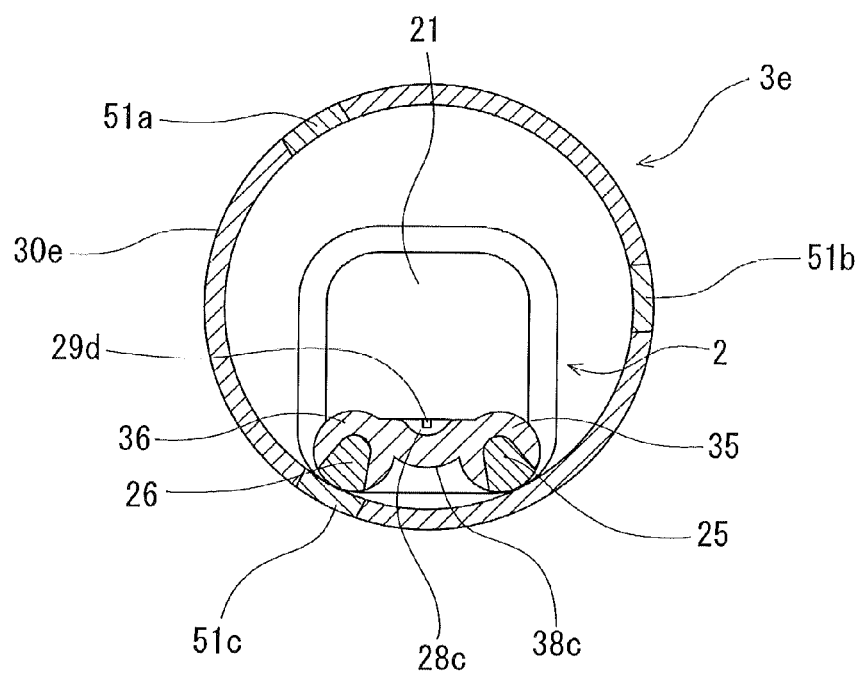
FIG. 22 is a cross-sectional enlarged view of an egg cryopreservation tool in which the tubular accommodation member shown in FIG. 21 is used.

As a mode of the heat conductive member, like a cell cryopreservation tool of an embodiment shown in FIGS. 21 and 22, the heat conductive member may be constructed as an axially extended linear one embedded in a side surface of a tubular accommodation member 3e. As shown in FIGS. 21 and 22, in this embodiment, a plurality of heat conductive members 51a, 51b, and 51c (specifically, two to six heat conductive members are provided. Three heat conductive members are provided in this embodiment) extended axially in parallel with the axis of a tubular accommodation member 30e is embedded in a tubular body 30e thereof. The embedded linear heat conductive members 51a, 51b, and 51c are exposed at the inner surface of the tubular accommodation member 3e and are capable of contacting the exposed side surfaces of the heat conductors 25, 26 of the cell holding member 2, as shown in FIG. 22.

The cell cryopreservation tool 1 of this embodiment has the lid member 4 to be mounted on the open portion of the tubular accommodation member 3. The lid member 4 has a lid body part 41 having a concave portion 43 to be mounted on the end of the open portion of the tubular accommodation member 3 and an extended portion 42 which is extended a predetermined length from a lower surface of the lid body part 41 and capable of penetrating into the tubular accommodation member 3. As shown in FIG. 1, by mounting the lid member 4 on the open portion of the tubular accommodation member 3, it is possible to prevent the cell holding member 2 from separating from the inside of the tubular accommodation member 3 and restrain the cell holding member 2 from moving inside the cell cryopreservation tool 1.

The method of using the cell cryopreservation tool 1 of the present invention is described below.

In the description made below, a case in which ova which are living cells are frozen and stored is exemplified.

Initially an operation of collecting a plurality of ova and replacing intracellular fluids of ova with equilibrium solutions is performed. Thereafter an operation of replacing extracellular fluids with vitrifying liquids is performed. After the ova are disposed at each of the cell accommodation concave portions 28a, 28b, 28c, 28d, and 28e formed on the cell attaching and holding portion 22 of the cell holding member 2 together with a small amount of the vitrifying liquid under a microscope, the ova are attached to the cell accommodation concave portions. The cell holding member 2 to which the ova have attached is inserted into the tubular accommodation member 3 from the side thereof where the cell attaching and holding portion 22 is disposed to bring the exposed portion of the heat conductors 25, 26 of the cell attaching and holding portion 22 of the cell holding member 2 into contact with the inner surface of the tubular accommodation member 3. Thereafter the tubular accommodation member 3 accommodating the cell holding member 2 is immersed in liquid nitrogen prepared in advance from the distal side of the tubular accommodation member 3 to freeze (vitrify) the ova. Owing to the contact between the liquid nitrogen and the tubular accommodation member 3, the tubular accommodation member 3 is rapidly cooled. The tubular accommodation member 3 which has been cooled quickly takes the temperature from the heat conductors 25, 26 of the cell attaching and holding portion 22 of the cell holding member 2 because the heat conductors 25, 26 are in contact with the inner surface of the tubular accommodation member 3. As a result, the ova held by the cell attaching and holding portion 22 is quickly cooled. As necessary, after the lid member 4 is mounted on the open portion of the tubular accommodation member 3, the tubular accommodation member 3 accommodating the cell holding member 2 holding the vitrified ova which have attached thereto is accommodated in an accommodation container (cane). Thereafter the accommodation container is put in a liquid nitrogen tank to store the ova.

INDUSTRIAL APPLICABILITY

The cell cryopreservation tool of the present invention is as described below.

(1) A cell cryopreservation tool comprising: a cell holding member having a body part formed of a cold-resistant material and a cell holding part formed of said cold-resistant material; and a tubular accommodation member, closed at one end thereof, which is capable of accommodating said cell holding member and formed of said cold-resistant material, wherein said cell holding part of said cell holding member has a long and narrow cell attaching and holding portion; said cell attaching and holding portion has a heat conductor extended in a longitudinal direction thereof; when said cell holding member is accommodated in said tubular accommodation member, said heat conductor is capable of contacting an inner surface of said tubular accommodation member.

In the cell cryopreservation tool of the present invention, after cells (for example, ova) treated with the cryopreservation liquid are sucked and disposed on the cell attaching and holding portion of the cell holding member, the cell holding member which holds the cells is inserted into the tubular accommodation member. Thereby the cells held by the cell holding member are protected by the tubular accommodation member and are not exposed to the outside.

Thereafter by bringing the tubular accommodation member which accommodates the cell holding member into contact with the cooling medium (for example, liquid nitrogen) with the distal side of the tubular accommodation member facing downward and performing an operation of preventing the liquid nitrogen from flowing into the tubular accommodation member, the tubular accommodation member is cooled, and further the heat conductor of the cell holding member in contact with the tubular member is also cooled. Thereby the cell holding member and the cells which have attached thereto are quickly cooled. Therefore the cell cryopreservation tool of the present invention allows the operation of placing the cells on the cell storing instrument to be accomplished easily and the cells to be frozen without bringing them into direct contact with the cooling medium.

The embodiments of the present invention may be carried out as described below.

(2) A cell cryopreservation tool according to the above (1), wherein said tubular accommodation member has a heat conductive member.

(3) A cell cryopreservation tool according to the above (2), wherein a part of said heat conductive member is exposed to an inner space of said tubular accommodation member; and when said cell holding member is accommodated inside said tubular accommodation member, said heat conductor of said cell holding member is capable of contacting an exposed portion of said heat conductive member.

(4) A cell cryopreservation tool according to any one of the above (1) through (3), wherein said heat conductor is provided at one side or both sides of said cell attaching and holding portion in such a way that said heat conductor is extended from a distal portion of said cell attaching and holding portion to a proximal side thereof.

(5) A cell cryopreservation tool according to any one of the above (2) through (4), wherein said heat conductive member is provided at a distal portion of said tubular accommodation member.

(6) A cell cryopreservation tool according to any one of the above (2) through (4), wherein said heat conductive member is provided on a side surface of said tubular accommodation member.

(7) A cell cryopreservation tool according to any one of the above (1) through (6), wherein said heat conductor is provided at both sides of said cell attaching and holding portion in such a way that said heat conductor is extended from a distal portion of said cell attaching and holding portion to a proximal side thereof.

(8) A cell cryopreservation tool according to any one of the above (1) through (7), wherein said cell attaching and holding portion has a cell accommodation concave portion; and said heat conductor is disposed essentially at one side or both sides of a portion of said cell attaching and holding portion where said cell accommodation concave portion is formed.

(9) A cell cryopreservation tool according to the above (8), wherein said cell attaching and holding portion has a groove portion communicating with said cell accommodation concave portion.

(10) A cell cryopreservation tool according to any one of the above (1) through (9), wherein said cold-resistant material is a liquid nitrogen-resistant material.

(11) A cell cryopreservation tool according to any one of the above (1) through (10), wherein said heat conductor is formed of metal, heat conductive ceramics or heat conductive plastics.

(12) A cell cryopreservation tool according to any one of the above (2) through (11), wherein said heat conductive member is formed of metal, heat conductive ceramics or heat conductive plastics.

The invention claimed is:

1. A cell cryopreservation tool comprising:
    a cell holding member having a body part formed of a liquid nitrogen-resistant material and a cell holding part formed of said liquid nitrogen-resistant material;
    an accommodation tube, closed at one end thereof, which is capable of accommodating said cell holding member, and wherein said accommodation tube has a tubular body formed of said liquid nitrogen-resistant material;
    said cell holding part of said cell holding member has an elongated cell attaching and holding portion;
    said cell attaching and holding portion has a first metal heat conductor extending in a longitudinal direction thereof and provided at one side or both sides of said cell attaching and holding portion;
    said first metal heat conductor has an exposed portion exposed from said cell holding member;
    said accommodation tube has a second metal heat conductor and a distal-end closed portion to prevent cooling medium from entering;
    said second metal heat conductor has an inner side exposed part exposed to an inner space of said accommodation tube; and
    when said cell holding member is accommodated in said accommodation tube, said exposed portion of said first metal heat conductor of said cell holding member contacts said inner exposed part of said second metal heat conductor in said accommodation tube.

2. The cell cryopreservation tool according to claim 1, wherein said second metal heat conductor has an outer side exposed part exposed to an outer space of said accommodation tube.

3. The cell cryopreservation tool according to claim 1, wherein said first metal heat conductor of said cell holding member extends from a distal portion of said cell attaching and holding portion to a proximal side of said cell attaching and holding portion.

4. The cell cryopreservation tool according to claim 1, wherein said second metal heat conductor is provided at a distal portion of said accommodation tube.

5. The cell cryopreservation tool according to claim 1, wherein said second metal heat conductor is provided on a side surface of said accommodation tube.

6. The cell cryopreservation tool according to claim 1, wherein said first metal heat conductor is provided at both sides of said cell attaching and holding portion in such a way that said first metal heat conductor is extended from a distal portion of said cell attaching and holding portion to a proximal side of said cell attaching and holding portion.

7. The cell cryopreservation tool according to claim 1, wherein said cell attaching and holding portion has a cell accommodation concave portion; and
    said first metal heat conductor is disposed essentially at one side or both sides of a portion of said cell attaching and holding portion where said cell accommodation concave portion is formed.

8. The cell cryopreservation tool according to claim 1, wherein said cell holding part has a rectangular cross section.

9. The cell cryopreservation tool according to claim 1, wherein said liquid nitrogen-resistant material is a synthetic resin, and wherein said synthetic resin is 3-polyethylene fluoride, low-density polyethylene, medium-density polyethylene, high-density polyethylene, polycarbonate, nylon, polysulfone, polyester, polystyrene, polyimide, ultra-high-molecular weight polyethylene, ethylene-vinyl acetate copolymer, or laminates of films formed of said synthetic resin.

10. The cell cryopreservation tool according to claim 1, wherein said cell holding part is transparent or semitransparent.

11. The cell cryopreservation tool according to claim 1, wherein said cell holding part has a width of 0.4 mm to 1.0 mm and a length of 5 mm to 30 mm, and wherein said body part has a length of 20 mm to 100 mm.

12. The cell cryopreservation tool according to claim 1, wherein said tubular body is transparent or semitransparent.

* * * * *